United States Patent
Lim

(10) Patent No.: US 9,863,762 B2
(45) Date of Patent: Jan. 9, 2018

(54) METHOD OF MANUFACTURING LIQUID CRYSTAL DISPLAY DEVICE AND INSPECTION DEVICE

(71) Applicant: Samsung Display Co., Ltd., Yongin-si (KR)

(72) Inventor: Yong-Woon Lim, Seoul (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 0 days.

(21) Appl. No.: 14/952,116

(22) Filed: Nov. 25, 2015

(65) Prior Publication Data

US 2016/0320178 A1    Nov. 3, 2016

(30) Foreign Application Priority Data

Apr. 30, 2015    (KR) .................. 10-2015-0061606

(51) Int. Cl.
*F23Q 23/08*     (2006.01)
*F23Q 23/10*     (2006.01)
(Continued)

(52) U.S. Cl.
CPC ......... *G01B 11/26* (2013.01); *G01N 21/8806* (2013.01); *G01N 21/95* (2013.01); *G02F 1/1337* (2013.01); *G02F 1/1341* (2013.01); *G02F 1/133528* (2013.01); *G01N 2021/8841* (2013.01); *G01N 2021/9513* (2013.01)

(58) Field of Classification Search
CPC . G01B 11/26; G02F 1/1341; G02F 1/133528; G02F 1/1337; G01N 2021/9513; G01N 21/95
See application file for complete search history.

(56) References Cited

U.S. PATENT DOCUMENTS

| 5,189,536 A * | 2/1993 | Hanyu ................ G02F 1/1416 345/97 |
| 2003/0048401 A1* | 3/2003 | Hanaoka .......... G02F 1/133753 349/123 |

(Continued)

FOREIGN PATENT DOCUMENTS

| KR | 19960024255 | 7/1996 |
| KR | 1019960024510 | 7/1996 |

(Continued)

OTHER PUBLICATIONS

Russell A . Chipman, "Polarimetry", Chapter 22, Optical Instruments. (1989), pp. 1-37.

*Primary Examiner* — Donald Raleigh
(74) *Attorney, Agent, or Firm* — Cantor Colburn LLP

(57) ABSTRACT

A method of manufacturing a liquid crystal display device according to an exemplary embodiment of the invention includes forming field generating electrodes on at least one of a lower display substrate and an upper display substrate, forming alignment layers on the lower display substrate and the upper display substrate, forming a liquid crystal layer including liquid crystal molecules between the lower display substrate and the upper display substrate, electric-field exposing the liquid crystal layer to pretilt the liquid crystal molecules of the liquid crystal layer, and measuring pretilt angles of the liquid crystal molecules after the electric-field exposing.

8 Claims, 10 Drawing Sheets

(51) Int. Cl.
  *G01B 11/26* (2006.01)
  *G02F 1/1341* (2006.01)
  *G02F 1/1337* (2006.01)
  *G02F 1/1335* (2006.01)
  *G01N 21/95* (2006.01)
  *G01N 21/88* (2006.01)

(56) References Cited

U.S. PATENT DOCUMENTS

| | | | | |
|---|---|---|---|---|
| 2010/0199547 A1* | 8/2010 | Reed | ............ | B01F 3/0807 |
| | | | | 44/354 |
| 2010/0225571 A1 | 9/2010 | Sakariya | | |
| 2011/0298833 A1 | 12/2011 | Dorjgotov et al. | | |
| 2012/0116045 A1* | 5/2012 | Kwak | ............ | C09K 19/56 |
| | | | | 528/170 |
| 2012/0172540 A1* | 7/2012 | Yang | ............ | C09K 19/56 |
| | | | | 525/421 |
| 2012/0249940 A1* | 10/2012 | Choi | ............ | G02F 1/133753 |
| | | | | 349/123 |
| 2013/0083278 A1* | 4/2013 | Teraoka | ............ | C08G 73/10 |
| | | | | 349/127 |
| 2014/0092348 A1* | 4/2014 | Muramatsu | ............ | G02F 1/13363 |
| | | | | 349/99 |
| 2014/0204322 A1* | 7/2014 | Miyake | ............ | G02F 1/1337 |
| | | | | 349/123 |
| 2015/0146155 A1* | 5/2015 | Engel | ............ | C09K 19/12 |
| | | | | 349/183 |
| 2015/0153619 A1* | 6/2015 | Murata | ............ | G02F 1/1337 |
| | | | | 349/123 |
| 2015/0267119 A1* | 9/2015 | Baron | ............ | C09K 19/3066 |
| | | | | 349/182 |
| 2016/0200976 A1* | 7/2016 | Jeong | ............ | G02F 1/1341 |
| | | | | 349/139 |
| 2016/0231603 A1* | 8/2016 | Zhang | ............ | G02F 1/1337 |
| 2016/0320178 A1* | 11/2016 | Lim | ............ | G01B 11/26 |

FOREIGN PATENT DOCUMENTS

| | | |
|---|---|---|
| KR | 1019980010358 | 4/1998 |
| KR | 1020000000875 | 1/2000 |
| KR | 1020010032656 | 4/2001 |
| KR | 100306644 | 8/2001 |
| KR | 100312787 | 10/2001 |
| KR | 1020020034221 | 5/2002 |
| KR | 100349586 | 8/2002 |
| KR | 100365496 | 12/2002 |
| KR | 100375309 | 2/2003 |
| KR | 1020030038897 | 5/2003 |
| KR | 100392471 | 7/2003 |
| KR | 1020030073071 | 9/2003 |
| KR | 100418922 | 2/2004 |
| KR | 1020040021464 | 3/2004 |
| KR | 1020040043220 | 5/2004 |
| KR | 100487309 | 4/2005 |
| KR | 100499520 | 6/2005 |
| KR | 1020050088833 | 9/2005 |
| KR | 1020050096999 | 10/2005 |
| KR | 100535348 | 12/2005 |
| KR | 1020050123158 | 12/2005 |
| KR | 1020060000594 | 1/2006 |
| KR | 100556383 | 2/2006 |
| KR | 1020060014253 | 2/2006 |
| KR | 1020060085543 | 7/2006 |
| KR | 100618670 | 8/2006 |
| KR | 100672421 | 1/2007 |
| KR | 100674924 | 1/2007 |
| KR | 1020070000120 | 1/2007 |
| KR | 100688505 | 2/2007 |
| KR | 100697380 | 3/2007 |
| KR | 1020070039093 | 4/2007 |
| KR | 1020070042803 | 4/2007 |
| KR | 1020070058827 | 6/2007 |
| KR | 100756734 | 9/2007 |
| KR | 1020070101712 | 10/2007 |
| KR | 100781306 | 11/2007 |
| KR | 100800736 | 1/2008 |
| KR | 1020080000143 | 1/2008 |
| KR | 1020080025556 | 3/2008 |
| KR | 100820355 | 4/2008 |
| KR | 1020080034881 | 4/2008 |
| KR | 100832289 | 5/2008 |
| KR | 100840672 | 6/2008 |
| KR | 1020080061196 | 7/2008 |
| KR | 1020080104480 | 12/2008 |
| KR | 1020080105642 | 12/2008 |
| KR | 1020080105977 | 12/2008 |
| KR | 1020090058712 | 6/2009 |
| KR | 1020090062706 | 6/2009 |
| KR | 100912116 | 8/2009 |
| KR | 1020090085282 | 8/2009 |
| KR | 100936788 | 6/2010 |
| KR | 100963799 | 6/2010 |
| KR | 100985205 | 9/2010 |
| KR | 101013988 | 2/2011 |
| KR | 1020110013243 | 2/2011 |
| KR | 1020110045259 | 5/2011 |
| KR | 1020120024829 | 3/2012 |
| KR | 101148222 | 5/2012 |
| KR | 1020120082671 | 7/2012 |
| KR | 1020120120987 | 11/2012 |
| KR | 1020130037019 | 4/2013 |
| KR | 101396934 | 5/2014 |
| WO | 2010141739 | 12/2010 |

* cited by examiner

METHOD OF MANUFACTURING LIQUID CRYSTAL DISPLAY DEVICE AND INSPECTION DEVICE

This application claims priority to Korean Patent Application No. 10-2015-0061606 filed on Apr. 30, 2015, and all the benefits accruing therefrom under 35 U.S.C. §119, the content of which in its entirety is incorporated herein by reference.

BACKGROUND (a) Field

Exemplary embodiments of the invention relate to a method of manufacturing a liquid crystal display device and an inspection device.

(b) Description of the Related Art

A liquid crystal display ("LCD") is one of the most common types of flat panel displays currently in use. The LCD generally includes two display substrates with field generating electrodes, such as a pixel electrode and a common electrode, and a liquid crystal layer interposed therebetween. The LCD generates an electric field in a liquid crystal layer by applying voltage to the field generating electrodes, and determines the direction of liquid crystal molecules of the liquid crystal layer, and controls polarization of incident light through the generated electric field, thus displaying images.

The LCD device is manufactured through various process operations, such as a thin film transistor ("TFT") substrate process, an opposing substrate process, and a liquid crystal process. Each process influences a process factor affecting an influence to an image quality of the LCD device, so that the process factor may be changed according to a variable generated in the processes.

For example, gamma is expressed by a method of representing a difference in brightness recognized by the eyes of a person by a gray scale in a voltage-transmittance curve, and an inherent gamma characteristic of the LCD device is determined according to a manufacturing process of the LCD device.

SUMMARY

When a manufacturing process has an error, a gamma defect may be generated. Gamma is generally inspected by PLI gamma monitoring after the liquid crystal display ("LCD") device is manufactur 1ed, and a lot of time is consumed until a defect generation is recognized, so that a damage due to the defect generation may be large. Further, it is difficult to predict an interaction of each monitoring factor through the confirmation of an individual process significant difference, and it is possible to analyze only a significant difference of a facility of an individual process. Further, current inspection equipment requires long measurement time, and a measurement error is generated The invention has been made in an effort to provide a method of manufacturing an LCD device, which is capable of monitoring a defect during a manufacturing process of an LCD device, and an inspection device.

An exemplary embodiment of the invention provides a method of manufacturing an LCD device, including forming field generating electrodes on at least one of a lower display substrate and an upper display substrate, forming alignment layers on the lower display substrate and the upper display substrate, forming a liquid crystal layer including liquid crystal molecules between the lower display substrate and the upper display substrate, electric-field exposing the liquid crystal layer to pretilt the liquid crystal molecules of the liquid crystal layer, and measuring pretilt angles of the liquid crystal molecules after the electric-field exposing.

In an exemplary embodiment, the method may further include measuring tilt angles of the liquid crystal molecules after the electric field exposing.

In an exemplary embodiment, the method may further include fluorescence-exposing the liquid crystal layer after the measuring the tilt angles.

In an exemplary embodiment, the method may further include attaching polarizers to the lower display substrate and the upper display substrate after the measuring the pretilt angles.

In an exemplary embodiment, the measuring of the pretilt angles may include determining whether the measured pretilt angles are within a predetermined range. When the measured pretilt angles exceed the predetermined range, the method may further include analyzing pretilt angle influencing factors.

In an exemplary embodiment, the pretilt angle influencing factors may include a voltage intensity during the electric-field exposing, a light intensity during the electric-field exposing, and a width of a fine branch portion of a pixel electrode.

In an exemplary embodiment, the analyzing of the pretilt angle influencing factors may include analyzing an influence degree of the pretilt angle influencing factors and selecting an imputation process. The method may further include notifying an analysis result of the influence degree to the imputation process.

In an exemplary embodiment, the measuring the tilt angles may include determining whether the measured tilt angles are within a predetermined range. When the measured tilt angles exceed the predetermined range, the method may further include analyzing inclination angle influencing factors.

In an exemplary embodiment, the tilt angle influencing factors may include a channel length of a thin film transistor ("TFT") and a thickness of the alignment layer.

In an exemplary embodiment, the analyzing the tilt angle influencing factors may include analyzing an influence degree of the tilt angle influencing factors and selecting an imputation process. The method may further include notifying an analysis result of the influence degree to the imputation process.

Another exemplary embodiment of the invention provides an inspection device, including an optical source unit configured to output polarized light, and including first to fifth polarization state generators, and a light receiving unit configured to receive polarized light, which is output from the optical source unit and passes through a sample, and including first to fifth polarization state analyzers corresponding to the first to fifth polarization state generators.

In an exemplary embodiment, optical axes of the respective polarization state generators may cross at one reference point.

In an exemplary embodiment, an optical axis of the first polarization state generator may correspond to a vertical central axis of the optical source unit.

In an exemplary embodiment, optical axes of the second and third polarization state generators may be inclined with respect to the vertical central axis in a first direction by ±α based on the reference point. Optical axes of the fourth and fifth polarization state generators may be inclined with respect to the vertical central axis in a second direction by ±β based on the reference point. The first direction may be vertical to the vertical central axis, and the second direction may be vertical to the vertical central axis and the first direction.

In an exemplary embodiment, the α and the β may have a same value.

In an exemplary embodiment, the second and fourth polarization state generators and the third and fifth polarization state generators may generate orthogonal polarized light.

In an exemplary embodiment, the second and fourth polarization state generators may output polarized light, and then the third and fifth polarization state generators may output polarized light.

In an exemplary embodiment, each of the polarization state generators may include an optical source, a fixed polarizer, and a rotating retarder.

In an exemplary embodiment, each of the polarization state analyzers may include a camera, a fixed linear polarizer, and a rotating retarder.

According to the exemplary embodiment of the invention, it is possible to pre-monitor a gamma defect by an initial alignment or driving after the electric field exposing process. It is possible to pre-detect an imputation process, so that it is possible to take measures when a defect is generated. Further, a gamma defect is monitored during a manufacturing process of the LCD panel, so that gamma monitoring is not demanded in a shipment step, thereby solving waste of material and human resources.

The inspection device of the invention has short measurement time, so that the inspection device may be used for monitoring a gamma defect during a manufacturing process of the LCD panel, and improve measurement accuracy. In addition, there are advantageous effects which may be described and recognized throughout the specification.

BRIEF DESCRIPTION OF THE DRAWINGS

The above and other exemplary embodiments, advantages and features of this disclosure will become more apparent by describing in further detail exemplary embodiments thereof with reference to the accompanying drawings, in which.

DETAILED DESCRIPTION

Figure 1:
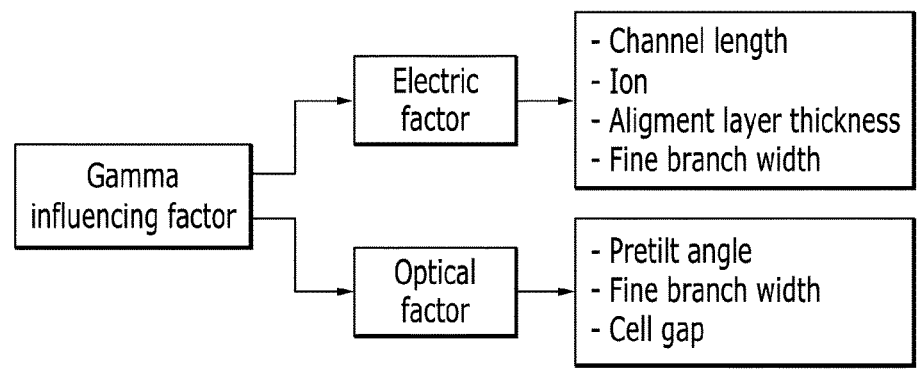
FIG. 1 is a block diagram illustrating a gamma influencing factor according to an exemplary embodiment of the invention.

The invention will be described more fully hereinafter with reference to the accompanying drawings, in which exemplary embodiments of the invention are shown. As those skilled in the art would realize, the described embodiments may be modified in various different ways, all without departing from the spirit or scope of the invention.

In the drawings, the thickness of layers, films, panels, regions, etc., are exaggerated for clarity. It will be understood that when an element such as a layer, film, region, or substrate is referred to as being "on" another element, it can be directly on the other element or intervening elements may also be present. In contrast, when an element is referred to as being "directly on" another element, there are no intervening elements present. Unless mentioned otherwise in the specification, "overlap" means overlap in a top plan view.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In the specification, terms "gamma", "a gamma value", and "a gamma conversion value" may be combined and used, all of the terms intend to represent a gamma conversion value unless defined otherwise, and a term, "gamma" will be mainly and simply used.

Gamma (γ) is obtained from a relationship between a gray scale and luminance, and an equation for obtaining gamma is represented below.

$$\text{Gamma} = \text{LOG}_{(\#Gray/Gray\_Max)}(LV\_\#Gray/LV\_Max)$$

Here, #Gray is a corresponding gray scale, Gray_Max is a maximum gray scale, LV_#Gray is luminance at a corresponding gray scale, and LV_Max is luminance at a maximum gray scale.

An adjustment of transmittance according to a gray scale to be appropriate to a person is referred to as a gamma adjustment, and gamma of about 2.2 is commonly considered to be most appropriate to the eyes of a person. It may be difficult to manufacture an LCD device to accurately have gamma of about 2.2 in every gray scale. Accordingly, when gamma at a gray scale of 20 to 200 is within about 2.2±0.2 in an LCD device expressing a gray scale of 256, the gamma may be considered to be included in an acceptable range.

FIG. 1 is a block diagram illustrating a gamma influencing factor according to an exemplary embodiment of the invention.

Gamma is determined according to luminance for each gray scale, so that a factor influencing luminance may be considered as a factor influencing a gamma variation (hereinafter, a gamma influencing factor). The factor may be divided into an electrical factor influencing a charge quantity of a liquid crystal capacitor and an optical factor influencing transmittance of the LCD device. The electrical factor includes a channel length of a TFT, an ion concentration, a thickness of an alignment layer, and the like, and the optical factor includes a pretilt angle, a width of a fine branch of a pixel electrode, a cell gap (a thickness of a liquid crystal layer), and the like. The factors may be changed according to a process variation to be considered as the gamma influencing factors. However, a metal thickness of a TFT, a width of a channel, and the like may also influence gamma as the electrical factors, but a variation amount thereof according to a process variation is weak, so that a metal thickness of a TFT, a width of a channel, and the like may be inappropriate as the gamma influencing factors. The electrical factor and the optical factor are not completely divided, but may have an interrelationship, and a specific factor (for example, a width of a fine branch) may correspond to the electrical factor and the optical factor.

Hereinafter, an LCD device according to the exemplary embodiment of the invention will be described in association with the aforementioned gamma influencing factor, and a method and a system for monitoring the gamma influencing factor in a manufacturing process of the LCD device will be described.

Figure 2:
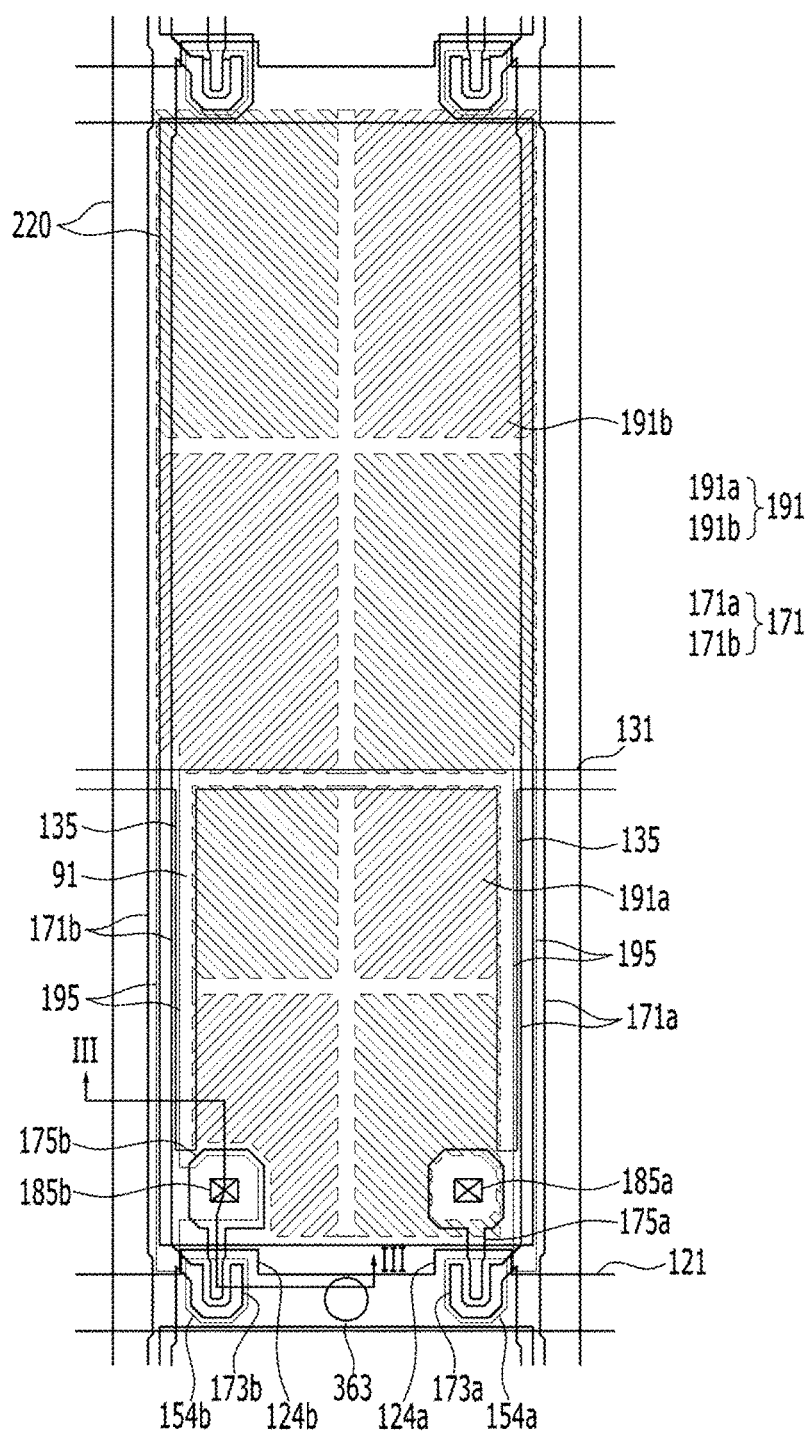
FIG. 2 is a plan view of an LCD device according to an exemplary embodiment of the invention.
Figure 3:
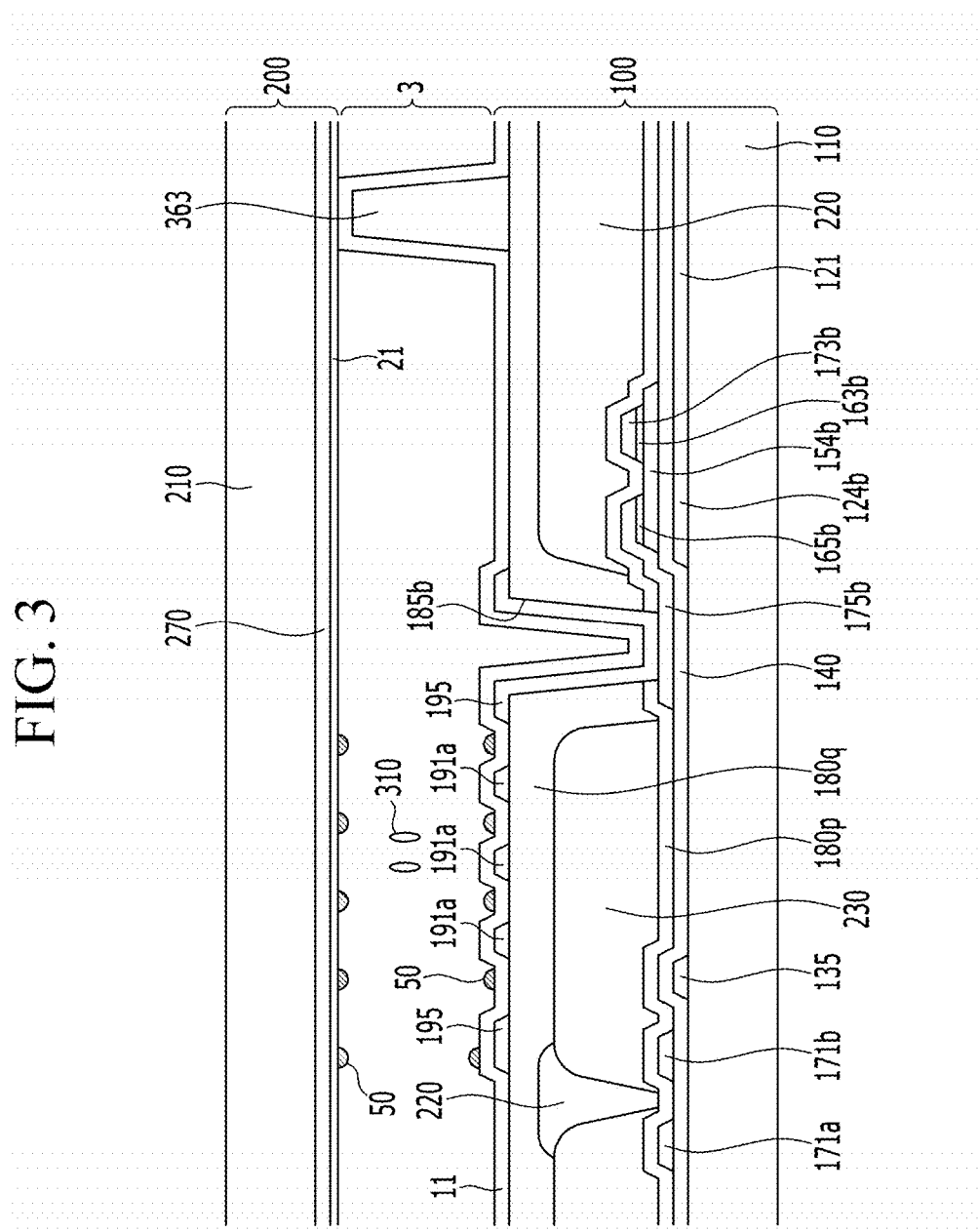
FIG. 3 is a cross-sectional view taken along line III-III of FIG. 2.

FIG. 2 is a plan view of an LCD device according to an exemplary embodiment of the invention, and FIG. 3 is a cross-sectional view taken along line III-III of FIG. 2.

Referring to FIGS. 2 and 3, the LCD according to the exemplary embodiment of the invention includes a lower display substrate 100 and an upper display substrate 200, which face each other, and a liquid crystal layer 3 interposed between the two display substrates 100 and 200. FIG. 1 approximately illustrates an area corresponding to one pixel, and the pixel may be arranged in a matrix form in the LCD device. A polarizer (not illustrated) may be attached onto an outer surface of the display substrates 100 and 200.

The lower display substrate 100 will be described. Gate conductors including a gate line 121 and storage electrode lines 131 and 135 are disposed on an insulating substrate 110 corresponding to a first substrate.

The gate line 121 transmits a gate signal and is mainly extended in a horizontal direction. The gate line 121 includes first and second gate electrodes 124a and 124b protruding in an up direction. The storage electrode lines 131 and 135 include a stem line 131 extended in substantially parallel to the gate line 121 and a storage electrode 135 extended from the stem line 131. A shape and a disposition of the gate conductor are not limited thereto, and may be changed in various forms.

A gate insulating layer 140 is disposed on the gate conductors, and semiconductors 154a and 154b including amorphous or crystalline silicon are positioned on the gate insulating layer 140.

Ohmic contacts are disposed on the semiconductors 154a and 154b. In an exemplary embodiment, the ohmic contacts may include a material, such as n+ hydrogenated amorphous silicon in which silicide or an n-type impurity is doped at a high concentration. The ohmic contacts exist only between the semiconductors 154a and 154b therebeneath and data lines 171a and 171b and drain electrodes 175a and 175b thereon, and reduce contact resistance therebetween. In the illustrated exemplary embodiment, referring to FIG. 3, ohmic contacts 163b and 165b are disposed on the semiconductor 154b, for example. In another exemplary embodiment, when the semiconductor is an oxide semiconductor, the ohmic contact may be omitted.

Data conductors including the data lines 171a and 171b and the first and second drain electrodes 175a and 175b are disposed on the ohmic contacts and the gate insulating layer 140. In the illustrated exemplary embodiment, referring to FIG. 3, the second drain electrode 175b is disposed on the ohmic contact 165b, for example.

The data lines 171a and 171b transmit a data signal, and are mainly extended in a vertical direction to cross the gate line 121 and the stem line 131 of the storage electrode line.

The data lines 171a and 171b include first and second source electrodes 173a and 173b extended toward the first and second gate electrodes 124a and 124b and bent in a U-shape, for example, and the first and second source electrodes 173a and 173b face the first and second drain electrodes 175a and 175b on the first and second gate electrodes 124a and 124b, respectively. One ends of the first and second drain electrodes 175a and 175b are partially surrounded by the first and second source electrodes 173a and 173b, respectively, and the other ends are provided to be wide to be connected with another layer. A shape and a disposition of the data conductor including the first and second drain electrodes 175a and 175b are not limited thereto, and may be changed in various forms.

The first and second gate electrodes 124a and 124b, the first and second source electrodes 173a and 173b, and the first and second drain electrodes 175a and 175b form first and second TFTs together with the first and second semiconductors 154a and 154b, and channels of the first and second TFTs are defined in the first and second semiconductors 154a and 154b between the first and second source electrodes 173a and 173b and the first and second drain electrodes 175a and 175b. An intensity of a drain current of the TFT is in proportion to a channel width and is in inverse-proportion to a channel length in a linear region. Among them, the channel length L may influence a charge quantity of a liquid crystal capacitor, and be changed according to a process variation, so that the channel length L is considered as the gamma influencing factor.

The semiconductors 154a and 154b include exposed portions, which are not covered with the data lines 171a and 171b and the drain electrodes 175a and 175b between the source electrodes 173a and 173b and the drain electrodes 175a and 175b. In an exemplary embodiment, a first passivation layer 180p including a silicon nitride (SiNx) or a silicon oxide (SiOx) is positioned on the data lines 171a and 171b, the drain electrodes 175a and 175b and the exposed portions of the semiconductors 154a and 154b, for example.

A color filter 230 is positioned on the first passivation layer 180p. The color filter 230 may display any one of the primary colors, such as three primary colors of red, green, and blue colors. The color filter 230 may also be disposed on the upper display substrate 200.

In an exemplary embodiment, a single layer or a dual layer including chromium and a chromium oxide, or a light blocking member 220 including an organic material is disposed on the color filter 230. Openings arranged in a matrix form may be defined in the light blocking member 220.

A second passivation layer 180q including a transparent organic material is disposed on the color filter 230 and the light blocking member 220. The second passivation layer 180q prevents the color filter 230 from being exposed and provides a flat surface. Contact holes 185a and 185b, through which the first and second drain electrodes 175a and 175b are exposed, is defined in the second passivation layer 180q. The second passivation layer 180q may also include an inorganic material.

A pixel electrode 191 is disposed on the second passivation layer 180q. In an exemplary embodiment, the pixel electrode 191 may include a transparent conductive material, such as an indium tin oxide ("ITO") or an indium zinc oxide ("IZO"), or a reflective metal, such as aluminum, silver, chromium, or an alloy thereof.

Figure 4:
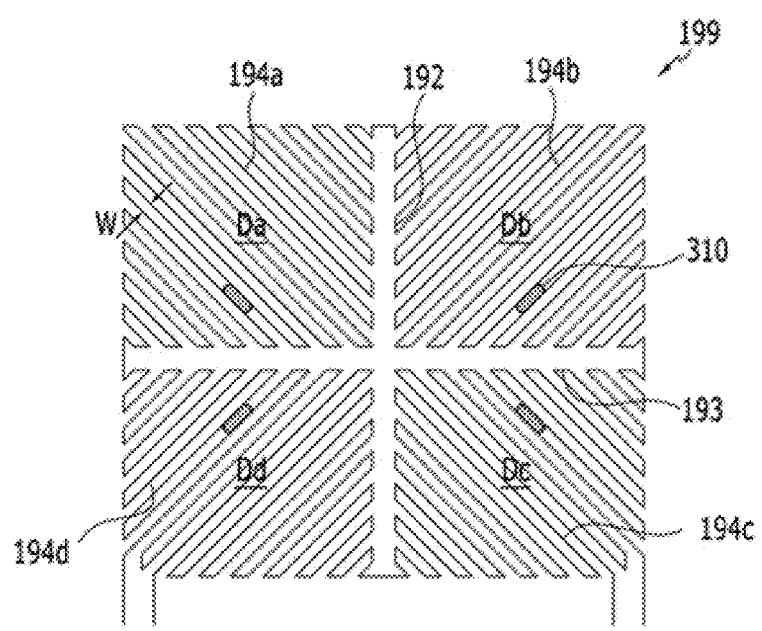
FIG. 4 is a top plan view illustrating an exemplary embodiment of a basic electrode of the LCD device according to the invention.

The pixel electrode 191 includes first and second subpixel electrodes 191a and 191b, which are separated from each other, and each of the first and second subpixel electrodes 191a and 191b includes one or more basic electrodes 199 illustrated in FIG. 4 or modifications thereof. A structure of the pixel electrode 191 will be described in more detail with reference to FIG. 4 below.

A lower alignment layer 11 is disposed on the pixel electrode 191. In an exemplary embodiment, the lower alignment layer 11 may be a vertical alignment layer.

A common electrode 270 is disposed on an entire surface of a transparent insulating substrate 210 corresponding to a second substrate on the upper display substrate 200. An upper alignment layer 21 is disposed on the common electrode 270. The upper alignment layer 21 may be a vertical alignment layer.

A liquid crystal layer 3 is disposed between the upper display substrate 200 and the lower display substrate 100. In an exemplary embodiment, the liquid crystal layer 3 includes the liquid crystal molecules 310 having negative dielectric anisotropy, for example. Long axes of the liquid crystal molecules 310 may be approximately vertical to the surfaces of the two display substrates 100 and 200 in a state where there is no electric field.

The liquid crystal layer 3 includes bumps 50 adjacently positioned to the alignment layers 11 and 21. The bump 50 includes an alignment polymer, which may be provided by irradiating light to reactive mesogen including an optical reactor. The bumps 50 pretilt the liquid crystal molecules. The alignment polymer may also be included in the alignment layers 11 and 21. The angle of the pretilt of the liquid crystal molecules may influence a gamma variation in, particularly, a low gray scale (for example, less than a gray scale of 100) and be changed according to a process variation, so that the angle of the pretilt of the liquid crystal molecules is considered as the gamma influencing factor.

A column spacer 363 is disposed between the upper display substrate 200 and the lower display substrate 100 in order to maintain a gap between the upper display substrate 200 and the lower display substrate 100. The column spacer 363 may maintain a thickness of the liquid crystal layer 3, that is, a cell cap. The cell gap may influence transmittance and be changed according to a process variation, so that the cell gap is considered as a gamma influencing factor.

Hereinafter, the basic electrode 199 of the pixel electrode 191 will be described in detail with reference to FIG. 4.

FIG. 4 is a top plan view illustrating the basic electrode of the LCD device according to the exemplary embodiment of the invention.

As illustrated in FIG. 4, the entire shape of the basic electrode 199 is a quadrangular shape, and the basic electrode includes a cross-shaped stem portion including a horizontal stem portion 193 and a vertical stem portion 192 that is approximately orthogonal to the horizontal stem portion 193. Further, the basic electrode 199 is divided into a first domain Da, a second domain Db, a third domain Dc, and a fourth domain Dd by the horizontal stem portion 193 and the vertical stem portion 192, and each of the domains Da, Db, Dc, and Dd includes a plurality of first to fourth fine branch portions 194a, 194b, 194c, and 194d.

The first fine branch portion 194a is extended obliquely in an upper left direction from the horizontal stem portion 193 or the vertical stem portion 192, and the second fine branch portion 194b is extended obliquely in an upper right direction from the horizontal stem portion 193 or the vertical stem portion 192. Further, the third fine branch portion 194c is extended obliquely in a lower right direction from the horizontal stem portion 193 or the vertical stem portion 192, and the fourth fine branch portion 194d is extended obliquely in a lower left direction from the horizontal stem portion 193 or the vertical stem portion 192. In an exemplary embodiment, the first to fourth fine branch portions 194a, 194b, 194c, and 194d form an angle of approximately 45 degrees (°) or approximately 135° to the gate line 121 or the horizontal stem portion 193, for example. In an exemplary embodiment, the fine branch portions 194a, 194b, 194c, and 194d of the two adjacent domains Da, Db, Dc, and Dd may be orthogonal to each other.

In an exemplary embodiment, a width W of the fine branch portions 194a, 194b, 194c, and 194d may be several micrometers, for example, about 2 micrometers to about 5 micrometers, for example. In an exemplary embodiment, a gap between the adjacent fine branch portions 194a, 194b, 194c, and 194d within one domain Da to Dd may also be several micrometers, for example, about 2 micrometers to about 5 micrometers. The width W of the fine branch portions 194a, 194b, 194c, and 194d may influence transmittance and a pretilt angle and be changed according to a process, so that the width W of the fine branch portions 194a, 194b, 194c, and 194d is considered as the gamma influencing factor.

Referring to FIGS. 1 and 4 together, each of the first and second subpixel electrodes 191a and 191b includes one basic electrode 199. An area of the second subpixel electrode 191b occupied in the entire pixel electrode 191 may be larger than an area of the first subpixel electrode 191a occupied therein, and for example, the basic electrodes 199 may be provided to have a different size, so that the area of the second subpixel electrode 191b is about 1 to about 2.2 times of the area of the first subpixel electrode 191a.

The second subpixel electrode 191b includes a pair of branches 195 extended along the data line 171. The branches 195 are positioned between the first subpixel electrode 191a and the data lines 171a and 171b, and connected at a lower end of the first subpixel electrode 191a. The first and second subpixel electrodes 191a and 191b are physically and electrically connected to the first and second drain electrodes 175a and 175b through the contact holes 185a and 185b, respectively, and receive a data voltage from the first and second drain electrodes 175a and 175b.

When a voltage is applied to the pixel electrode 191 and the common electrode 270, the liquid crystal molecules 310 respond to an electric field generated between the pixel electrode 191 and the common electrode 270, such that a direction of the long axes of the liquid crystal molecules 310 is changed into a direction that is vertical to a direction of the electric field. A degree of change in polarization of light incident to the liquid crystal layer 3 varies according to a degree of inclination of the liquid crystal molecules 310, the change in polarization is represented as a change in transmittance by a polarizer, and the LCD device displays an image through the change of the transmittance.

The direction, in which the liquid crystal molecules 310 are inclined, is determined by the fine branch portions 194a, 194b, 194c, and 194d of the pixel electrode 191, and the liquid crystal molecules 310 are inclined in a direction that is parallel to a longitudinal direction of the fine branch portions 194a, 194b, 194c, and 194d. One pixel electrode 191 includes the four domains Da, Db, Dc, and Dd, in which the longitudinal directions of the fine branch portions 194a, 194b, 194c, and 194d are different one another, so that the directions, in which the liquid crystal molecules 310 are inclined, are approximately four directions. As described above, it is possible to improve a viewing angle of the LCD device by varying the inclination direction of the liquid crystal molecules.

The first subpixel electrode 191a and the common electrode 270 form a first liquid crystal capacitor together with the liquid crystal layer 3 between the first subpixel electrode 191a and the common electrode 270, and the second subpixel electrode 191b and the common electrode 270 form a second liquid crystal capacitor together with the liquid crystal layer 3 between first subpixel electrode 191a and the common electrode 270 to maintain the applied voltage even after the first and the second TFTs Qa and Qb are turned off. The charge voltages of the two liquid crystal capacitors represent different gamma curves, and a gamma curve of one pixel voltage becomes a curve obtained by combining the gamma curves. The combined gamma curve at a front side is set to be identical to a reference gamma curve at the front surface, which is set to be most suitable, and the synthetic gamma curve at a lateral side is set to be closest to the reference gamma curve at the front side. The lateral side visibility is improved by changing the image data as described above. In addition, various technologies for varying the charge charged in the first liquid crystal capacitor and the second liquid crystal capacitor may be applied to the invention.

The first and second subpixel electrodes 191a and 191b overlap the storage electrode lines 131 and 135 to form first and second storage capacitors, and the first and second storage capacitors enhance voltage storage performance of the first and second liquid crystal capacitors, respectively.

Hereinafter, a method of manufacturing the LCD device according to the exemplary embodiment of the invention, and a method of monitoring the gamma influencing factor performed during the manufacturing process will be described.

Figure 5:
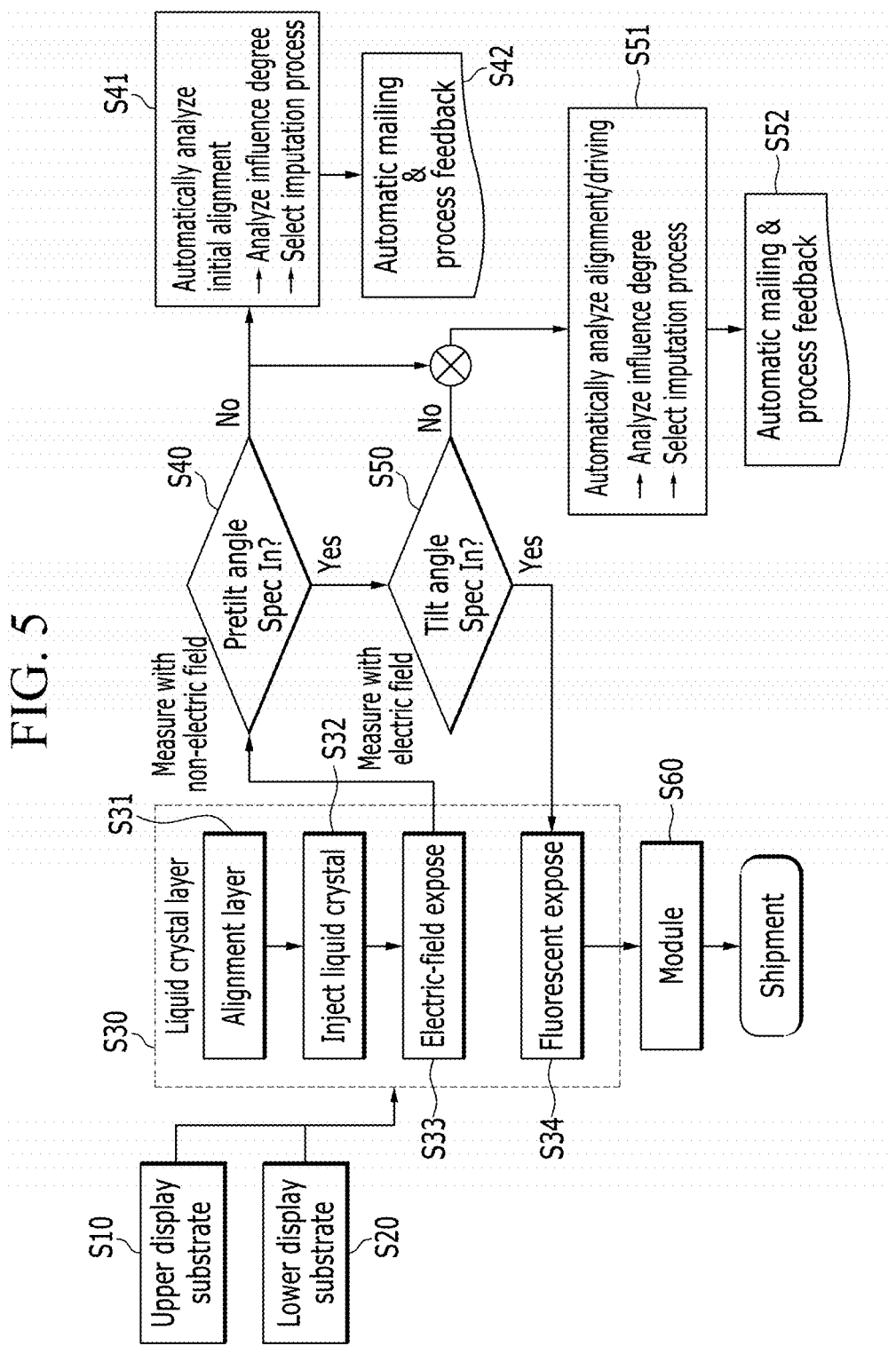
FIG. 5 is a block diagram illustrating an exemplary embodiment of a method of manufacturing the LCD device and a monitoring method according to the invention.

FIG. 5 is a block diagram illustrating a method of manufacturing the LCD device and a monitoring method according to an exemplary embodiment of the invention.

First, processes S10 and S20 of manufacturing the lower display substrate 100 and the upper display substrate 200 are manufactured, respectively, are performed.

The lower display substrate 100 may be manufactured by, for example, a method described below.

Gate conductors including gate lines 121 and gate electrodes 124a and 124b, a gate insulating layer 140, semiconductors 154a and 154b, data conductors including data lines 171a and 171b, source electrodes 173a and 173b, and drain electrodes 175a and 175b, and a first passivation layer 180p are sequentially provided by stacking a plurality of thin films on a substrate 110 and patterning the plurality of thin films.

Subsequently, a color filter 230 is disposed on the first passivation layer 180p, and a light blocking member 220 for blocking light leakage is disposed on the color filter 230. A second passivation layer 180q is disposed on the light blocking member 220 and the color filter 230.

A pixel electrode 191 having a vertical step portion 192, a horizontal step portion 193, and a plurality of fine branch portions 194a, 194b, 194c, and 194d extended from the vertical step portion 192 and the horizontal step portion 193 is provided by stacking a transparent conductive layer, such as an ITO or an IZO, on the second passivation layer 180q and patterning the transparent conductive layer. A column spacer 363 is disposed on the second passivation layer 180q or the pixel electrode 191.

The upper display substrate 200 may be manufactured by forming a common electrode 170 on an insulating substrate 210. According to the exemplary embodiment, the color filter 230 and/or the light blocking member 220 may also be disposed on the insulating substrate 210.

A process S30 of forming a liquid crystal layer 3 is performed after manufacturing each of the lower display substrate 100 and the upper display substrate 200, and as a result, an LCD panel, in which the liquid crystal layer 3 is disposed between the two display substrates 100 and 200, is manufactured. The process of forming the liquid crystal layer 3 includes an alignment layer forming process S31, a liquid crystal injecting process S32, an electric field exposing process S33, and a fluorescent exposing process S34. In another exemplary embodiment, the fluorescent exposing process S34 may be omitted.

In the alignment layer forming process S31, the alignment layers 11 and 21 may be provided by applying an alignment layer forming material, such as a polyimide solution, onto the pixel electrode 191 of the lower display substrate 100 and the common electrode 270 of the upper display substrate 200 and performing a heat treatment on the alignment layer forming material.

Next, a process S32 of bonding the lower display substrate 100 and the upper display substrate 200, and injecting a liquid crystal material including reactive mesogen, between the two display substrates 100 and 200 is performed. However, the liquid crystal layer 3 may also be provided by dropping a liquid crystal material onto the lower display substrate 100 or the upper display substrate 200, and then bonding the lower display substrate 100 and the upper display substrate 200.

Next, the electric field exposing process S33 is performed. The electric field exposing process S33 includes irradiating light, such as ultraviolet rays ("UV"), to the LCD panel in a state where voltages are applied to the pixel electrode 191 and the common electrode 270. Then, the reactive mesogen is inclined in a direction approximately parallel to the longitudinal directions of the fine branch portions 194a to 194d of the pixel electrode 191 together with the liquid crystal molecules 310 while moving toward the display substrates 100 and 200 and forms an alignment polymer to form bumps 50. The liquid crystal molecules 310 have pretilts by the bumps 50 provided as described above. Accordingly, the liquid crystal molecules 310 are arranged to have pretilts in four different directions even in a state where voltages are not applied to the pixel electrode 191 and the common electrode 270. The liquid crystal molecules 310 have the pretilts, so that when voltages are applied, the liquid crystal molecules 310 are rapidly inclined in pretilt directions, thereby implementing a fast response speed. When the reactive mesogen is included in the alignment layer, the alignment polymer may also be provided in the alignment layer. The reactive mesogen, which fails to form the alignment polymer and remains, may be removed through the fluorescent exposing process S34.

According to the exemplary embodiment, a measuring process S40 with a non-electric field and a measuring process S50 with an electric field are performed during the liquid crystal layer forming process S30, for example, after the electric field exposing process S33 and before the fluorescent exposing process S34. The two processes correspond to a gamma monitoring process, and through the gamma monitoring process, it is possible to analyze the gamma influencing factor, find a defect early, and take measures during the manufacturing process of the LCD device. It is exemplified that the measuring process S50 with the electric field is performed after the measuring process S40 with the non-electric field, but the order thereof may be changed.

In the measuring process S40 with the non-electric field, the pretilt angles of the liquid crystal molecules are measured by using an inspection device in a state where voltages are not applied to the pixel electrode 191 and the common electrode 270. When an electric field is not applied to the liquid crystal layer 3, the liquid crystal molecules have the pretilts and are in an initially alignment state, so that it is possible to measure the pretilt angles of the liquid crystal molecules.

When the measured pretilt angles are within a predetermined range, a probability that a gamma defect is generated by the pretilt angles is low, so that measuring process S50 with the electric field is performed. However, when the measured pretilt angles exceed the predetermined range, a gamma defect may be caused. Particularly, the pretilt angles may considerably influence a low gray scale gamma because the pretilt angles are highly related with black luminance, a side contrast ratio, and the like. Accordingly, when the pretilt angles exceed the predetermined range, an automatic initial alignment analysis S41 of analyzing a factor influencing the pretilt angles may be performed. The automatic initial alignment analysis S41 may be automatically performed by, for example, receiving, by an analysis device, measurement data from the inspection device and performing an analysis through an influencing factor analyzing program.

The pretilt angle influencing factors include a voltage intensity during the electric field exposure, a light intensity during the electric field exposure, a width of the fine branch portion of the pixel electrode, and the like. In the automatic initial alignment analysis S41, an influence degree of the influencing factors may be analyzed, and an imputation process may be selected based on a result of the analysis. The kind of factor, a degree of influence of a specific factor may be managed through a database. When the number of pretilt angle influencing factors is two or more, a priority of the pretilt angle influencing factors may also be set.

An influence degree analysis result may be automatically mailed to the imputation process. An engineer of a corresponding process may correct an error requiring a process management based on the influencing degree analysis result and the like. In an exemplary embodiment, an intensity of light during the electric field exposure in the analysis of the influencing degree exceeds a reference value (processing margin), so that when it is evaluated that an error is generated in the pretilt angle, an engineer of an electric field exposure process may take measures of adjusting the intensity of light to be included within the reference value. The measures are performed during the manufacturing process of the LCD device, thereby minimizing a defect from being generated.

In the measuring process S50 with the electric field, tilt angles of the liquid crystal molecules are measured by using the inspection device in a state where a voltage is applied to the pixel electrode 191 and the common electrode 270. When the measured tilt angles are within a predetermined range, a probability that a gamma defect is generated is low, so that the fluorescent exposure process S34 is performed. However, when the measured tilt angles exceed the predetermined range, a gamma defect may be caused, and particularly, an influence on a high gray scale gamma may be large. The tilt angles of the liquid crystal molecules is related to the alignment of the liquid crystal molecules generated during the driving of the LCD device, so that an automatic alignment/driving analysis S51 of analyzing a factor influencing the tilt angles when the measured tilt angles exceed the predetermined range may be performed. The automatic alignment/driving analysis S51 may be automatically performed by receiving, by the analysis device, measurement data from the inspection device and performing an analysis through the influencing factor analyzing program, similar to the automatic initial alignment analysis S41.

The tilt angle influencing factors may include a channel length of the TFT, a thickness of the alignment layer, and the like, and may also include a width of the fine branch portion of the pixel, a voltage intensity during the electric field exposure, an intensity of light during the electric field exposure, and the like. In the automatic alignment/driving analysis S51, an influence degree of the influencing factor may be analyzed, and an imputation process may be selected based on a result of the analysis. The kind of factor, a degree of influence of a specific factor may be managed through a database, and when the number of tilt angle influencing factors is two or more, a priority of the tilt angle influencing factors may also be set.

An influence degree analysis result may be automatically notified (e.g., mailed) to the imputation process (S52), and an engineer receiving the influence degree analysis result may correct an error requiring a process management. In an exemplary embodiment, when the channel length of the TFT exceeds a reference value by the analysis of the influence degree, so that it is evaluated that an error is generated in the tilt angles, an engineer of a lower display substrate process may inspect a photolithography process and take measures of correcting an error. The measures are performed during the manufacturing process of the LCD device, so that it is possible to rapidly take measures when a defect is generated, and minimize a generation of a defect.

The LCD panel, which is evaluated that the pretilt angles and the tilt angles of the liquid crystal molecules are within the reference values through the measuring process S40 with the non-electric field and the measuring process S50 with the electric field that are the gamma monitoring process, may be considered that gamma thereof is within a reference value. In the LCD panel, the reactive mesogen, which may be left in the liquid crystal layer, is removed through the fluorescent exposing process S34, so that a liquid crystal layer forming process is completed.

In a subsequent module process S60, a polarizer is attached onto the LCD panel, and a circuit board and the like, in which a driving device and the like is mounted, so that an LCD device is finally completed. The module process S60 is not performed on the LCD panel which is determined to have a defect in the aforementioned gamma monitoring process, and thus it is possible to prevent material resources from being wasted. Further, the completed LCD device has already undergone the monitoring of the gamma defect during the manufacturing process, so that it is not necessary to monitor gamma when the LCD device is forwarded.

Hereinafter, an inspection device, which is usable in the aforementioned gamma monitoring process, will be described.

Figure 6:
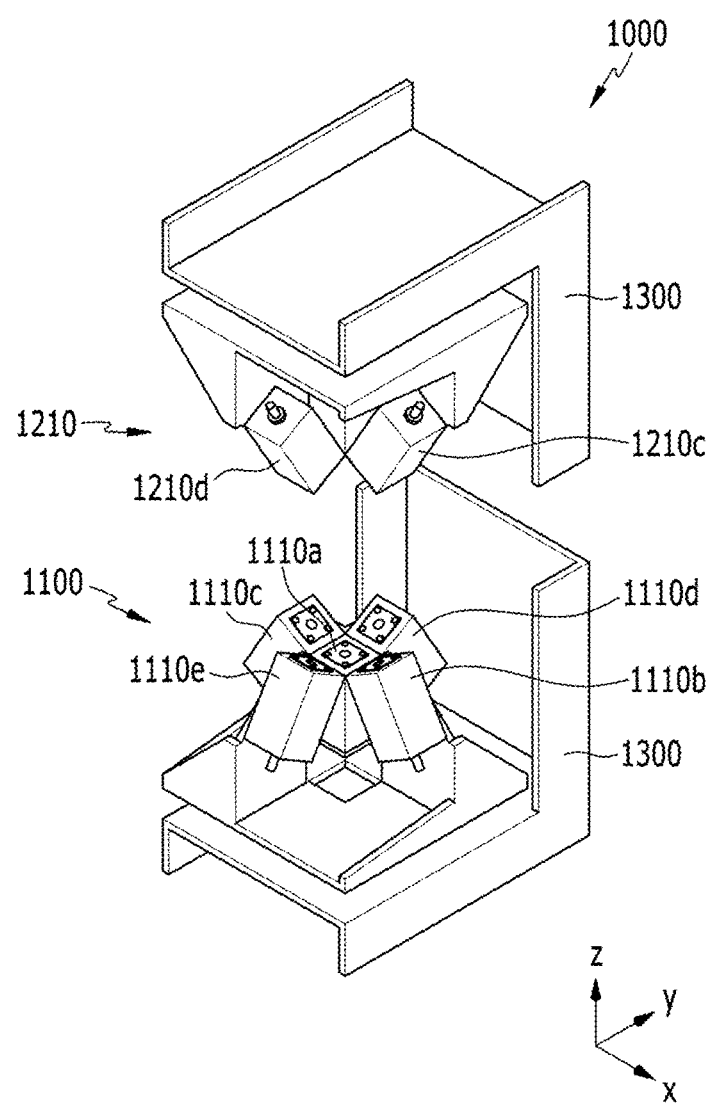
FIG. 6 is a schematic perspective view of an exemplary embodiment of an inspection device according to the invention.
Figure 7:
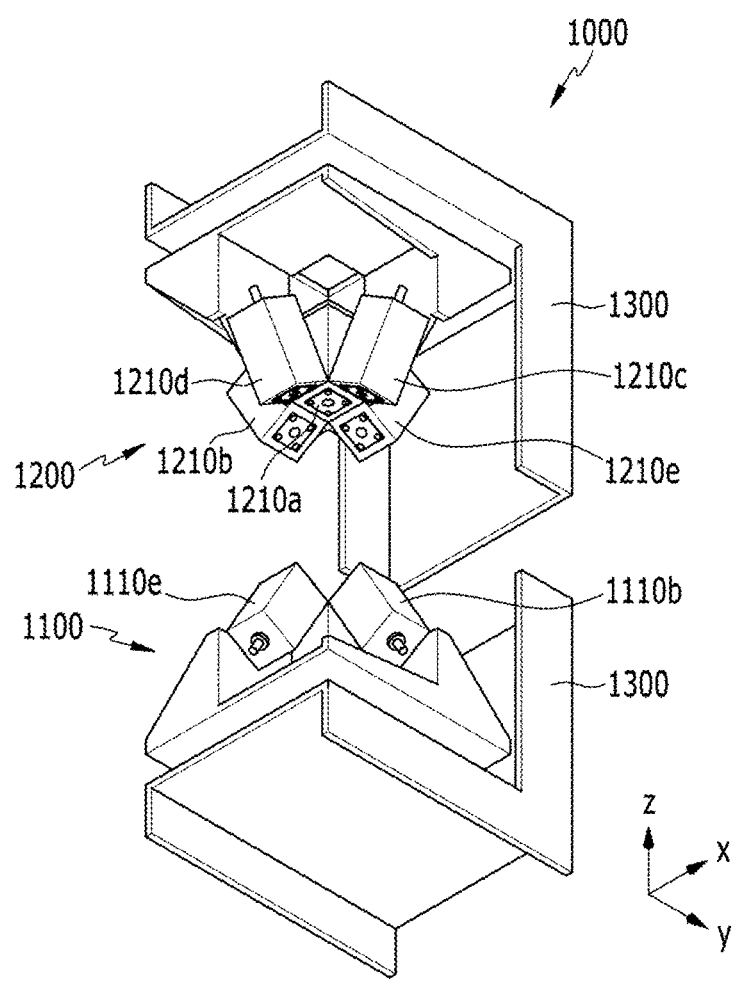
FIG. 7 is a perspective view of the inspection device of FIG. 6 viewed at a different angle.
Figure 8:
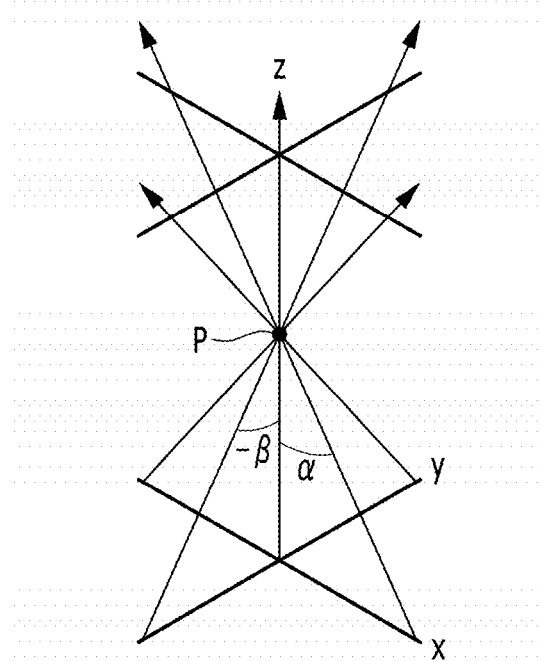
FIG. 8 is a diagram illustrating an optical axis in the inspection device of FIG. 6.
Figure 9:
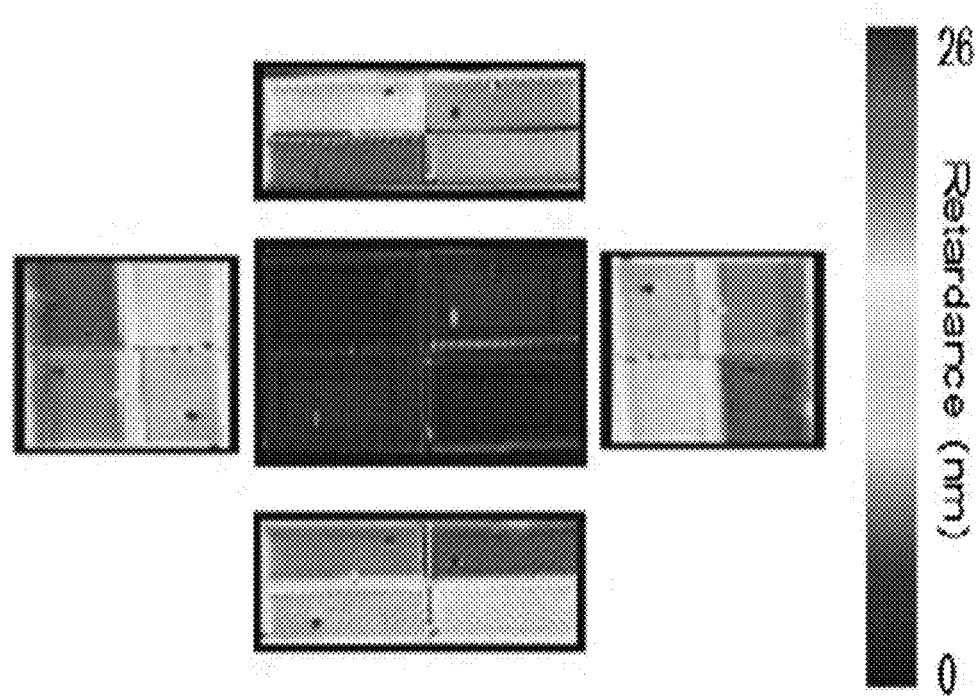
FIG. 9 is a diagram illustrating an image obtained by the inspection device of FIG. 6.
Figure 10:
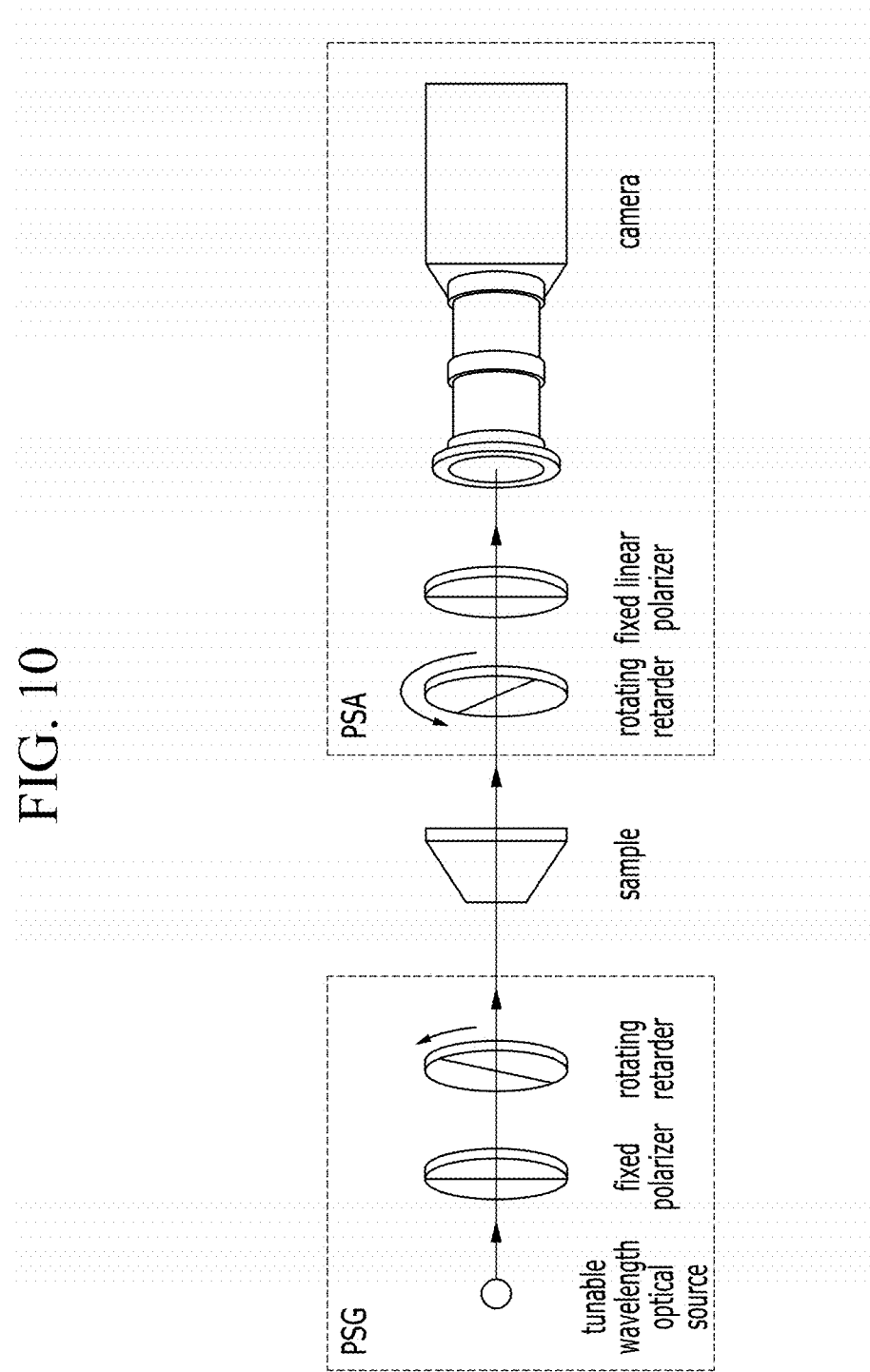
FIG. 10 is a diagram illustrating a configuration of a polarization state generator and a polarization state analyzer of the inspection device of FIG. 6.

FIG. 6 is a schematic perspective view of an inspection device according to an exemplary embodiment of the invention, FIG. 7 is a perspective view of the inspection device of FIG. 6 viewed at a different angle, FIG. 8 is a diagram illustrating an optical axis in the inspection device of FIG. 6, FIG. 9 is a diagram illustrating an image obtained by the inspection device of FIG. 6, and FIG. 10 is a diagram illustrating a configuration of a polarization state generator and a polarization state analyzer of the inspection device of FIG. 6.

Referring to FIGS. 6 and 7, an inspection device 1000 includes an optical source unit 1100 and a light receiving unit 1200 coupled to a lower part and an upper part of a holding stand 1300. The optical source unit 1100 and the light receiving unit 1200 are disposed to face each other, so that light emitted from the optical source unit 1100 is incident into the light receiving unit 1200. In order to measure a state of a sample (LCD panel) (not illustrated), the sample is substantially horizontally positioned between the optical source unit 1100 and the light receiving unit 1200. Accordingly, light emitted from the optical source unit 1100 passes through a part of the sample corresponding to a reference point P and then is incident into the light receiving unit 1200. The optical source unit 1100 may irradiate polarized light, such as linear polarized light, circular polarized light, and elliptical polarized light, to the sample, and the light receiving unit 1200 may capture the polarized light passing through the sample and obtain an image. The reference point P may be an area corresponding to one pixel or subpixel.

In the exemplary embodiment of the invention, the optical source unit 1100 includes five polarization state generators ("PSGs") 1110, and the light receiving unit 1200 includes five polarization state analyzers ("PSAs") 1210.

Based on a path (hereinafter, also referred to as an optical axis) of light emitted from each PSG 1110 and incident into the reference point P, the disposition of the five PSGs 1110a to 1110e of the optical source unit 1100 and the five PSAs 1210a to 1210e of the light receiving unit 1200 will be described with reference to FIGS. 6, 7, and 8.

First, the PSGs 1110a to 1110e will be described. The second to fifth PSGs 1110b to 110e are disposed around the first PSG 1110a, of which an optical axis corresponds to a z-axis, and optical axes of the PSGs 1110a to 1110e cross at the reference point P. Here, the z-axis may correspond to a vertical central axis of the optical source unit 1100. The optical axis of the second PSG 1110b is inclined with respect to the z-axis in an x-axis direction by +α based on the reference point P, and the optical axis of the third PSG 1110c is inclined with respect to the z-axis in the x-axis direction by −α based on the reference point P. The optical axis of the fourth PSG 1110d is inclined with respect to the z-axis in a y-axis direction by +β based on the reference point P, and the optical axis of the fifth PSG 1110e is inclined with respect to the z-axis by −β based on the reference point P. Accordingly, the second PSG 1110b and the third PSG 1110c may be symmetric to each other based on the first PSG 1110a, and the fourth PSG 1110d and the fifth PSG 1110e may also be symmetric to each other based on the first PSG 1110a. Here, a and 13 correspond to tilt angles (polar angles) of the optical axes of the second to fifth PSGs 1110b to 1110e, and may be the same as each other, and may be about 35°, for example. However, α and β are not limited thereto, and have various values, such as 33 and 37, so that α and β may be set, so that the optical axis is variously inclined. Further, the second to fifth PSGs 1110b to 1110e may be designed, so that a polar angle ±α and ±β is adjusted within a predetermined range, and may be various up to, for example, about 70°.

The PSAs 1210a to 1210e correspond one to one to the PSGs 1110a to 1110e, and are disposed to receive light emitted from the PSGs 1110a to 1110e, respectively. That is, similar to the disposition of the second to fifth PSGs 1110b to 1110e around the first PSG 1110a, the second to fifth PSAs 1210b to 1210e are disposed around the first PSA 1210a. Particularly, the first PSA 1210a is disposed on the optical axis of the first PSG 1110a, the second PSA 1210b is disposed on the optical axis of the second PSG 1110b, the third PSA 1210c is disposed on the optical axis of the third PSG 1110a, the fourth PSA 1210d is disposed on the optical axis of the fourth PSG 1110d, and the fifth PSA 1210e is disposed on the optical axis of the fifth PSG 1110e. Accordingly, the first to fifth PSAs 1210a to 1210e receive light, which is emitted from the first to fifth PSGs 1110a to 1110e, respectively, and then passes through the reference point P.

In order to measure an azimuthal angle in various axes, the second to fifth PSGs 1110b to 1110e and the second to fifth PSAs 1210b to 1210e corresponding to the second to fifth PSGs 1110b to 1110e may be designed, so that azimuthal angles thereof are rotatable. In an exemplary embodiment, a rotation may be a range of about 0° to about 90° for each set of PSG and PSA, and in this case, it is possible to measure all of the angles included within the azimuthal angle of 360° in four sets of PSG and PSA on the x-axis and the y-axis.

When it is possible to adjust the angles of the optical axes of the second to fifth PSGs 1110b to 1110e, the second to fifth PSAs 1210b to 1210e may be designed so as to be adjusted in accordance with the second to fifth PSGs 1110b to 1110e.

As described, when the inspection device is configured so that the optical source unit 1100 and the light receiving unit 1200 include the five PSGs 1110a to 1110e and the five PSAs 1210a to 1210e corresponding to the five PSGs 1110a to 1110e, respectively, it is possible to obtain images, for example, FIG. 9 (α and β are 35) measured at five angles at one time. Accordingly, measurement accuracy is increased, and particularly, it is possible to dramatically decrease a measurement time, compared to the case where an image is obtained at various angles by using one set of PSG and PSA (time is consumed in order to measure gamma at various angles, and a measurement point may be shifted for each image). The decrease of the measurement time means that the inspection device is usable as a monitoring device during the manufacturing process of the LCD device. When the measurement time is long, process time is increased, so that it is inappropriate to apply the inspection device to monitoring.

Further, the PSGs 1110a to 1110e and the PSAs 1210a to 1210e are biaxially disposed, so that it is possible to obtain an image from two axes at the same time, and it is possible to improve measurement accuracy compared to the measurement in one axis at various angles. During the measurement, when each of the second and third PSGs 1110b and 1110c and the fourth and fifth PSGs 1110d to 1110e sequentially makes an orthogonal polarization stage be incident into the reference point P, interference is not generated between the incident light, and a measurement error due to luminance variation is not generated in the obtained image. It is exemplified that the optical source unit 1100 and the light receiving unit include the fives PSGs 1110a to 1110e and the five PSAs 1210a to 1210e, but according to an exemplary embodiment, the optical source unit 1100 may include five or more PSGs, and the light receiving unit 1200 may include the PSAs having the number corresponding to the number of PSGs. In an exemplary embodiment, each of the optical source unit 1100 and the light receiving unit 1200 may include odd numbered PSGs and PSAs for symmetry of the measurement data, and may include 1+4n sets of PSG and PSA (here, n is a natural number). In an exemplary embodiment, the optical source unit 1100 may further include four PSGs, of which an optical axis is inclined in the x-axis or the y-axis direction at ±δ (for example, δ is about 45°), in addition to the aforementioned five PSGs 1110a to 1110e, and the light receiving unit 1200 may further include four PSAs corresponding to the additionally included four PSGs. In this case, it is possible to obtain an image at more angles, so that measurement accuracy is increased.

Referring to FIG. 10, detailed configurations of the PSG 1110 and the PSA 1210 will be described. The PSG 1110 includes an optical source, a fixed polarizer, and a rotating retarder. In an exemplary embodiment, the optical source may emit light of a specific wavelength, for example, visible light, of which a wavelength is tunable within a range of about 380 nanometers to about 780 nanometers. The light emitted from the optical source is converted into polarized light while passing through the fixed polarizer and the rotating retarder. In this case, linear polarized light, circular polarized light, or elliptical polarized light may be irradiated toward a sample positioned between the PSG 1110 and the PSA 1210 as input optical data by rotating the rotating retarder. Referring to FIGS. 10 and 6 together, in order to prevent an interference phenomenon between the second and third PSGs 1110b and 1110c positioned on the same axis and an interference phenomenon between the fourth and fifth PSGs 1110d and 1110e positioned on the same axis, the second and fourth PSGs 1110b and 1110d and the third and fifth PSGs 1110c and 1110e may irradiate orthogonal polarized light. In an exemplary embodiment, the second and fourth PSGs 1110b and 1110d may be combined so as to irradiate x-axis or y-axis linear polarized light and the third and fifth PSGs 1110c and 1110e may be combined so as to irradiate y-axis or x-axis linear polarized light (linear combination), and the second and fourth PSGs 1110b and 1110d may be combined so as to irradiate right circular polarized light or left circular polarized light and the third and fifth PSGs 1110c and 1110e may be combined so as to irradiate left circular polarized light or right circular polarized light (circular combination). Further, the second and fourth PSGs 1110b and 110d irradiate polarized light, and then the third and fifth PSGs 1110c and 1110e may irradiate polarized light (or in a reverse order).

The PSA 1210 includes a camera, a fixed linear polarizer, and a rotating retarder. Polarized light passing through and emitted from a sample passes through the rotating retarder and the fixed linear polarizer to be incident into the camera as output optical data, and the camera outputs the output optical data in a form of, for example, the image as illustrated in FIG. 9. In an exemplary embodiment, the camera may be a charge-coupled device ("CCD") camera, for example.

Various optical characteristics of the sample may be obtained through the Muller matrix interpretation of input optical data and output optical data. In an exemplary embodiment, the Muller matrix, which is 4×4 matrix, may be completed based on input optical data and output optical data expressed by a strokes vector, and a cell gap, a pretilt angle of the liquid crystal molecules, an tilt angle of the liquid crystal molecules, and an alignment direction of the liquid crystal molecules by fitting an optical value (for example, retardance and a position angle) obtained from the Muller matrix. In addition, it is possible to measure a rubbing angle of the alignment layer, a twist angle of the liquid crystal molecules, and the like. A technique for obtaining an optical characteristic by using the Muller matrix is known to the technical field in the art, so that a detailed description thereof will be omitted herein.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method of manufacturing a liquid crystal display device, the method comprising:
   forming field generating electrodes including a pixel electrode and a common electrode on at least one of a lower display substrate and an upper display substrate;
   forming alignment layers on the lower display substrate and the upper display substrate;
   forming a liquid crystal layer including liquid crystal molecules between the lower display substrate and the upper display substrate;
   electric-field exposing the liquid crystal layer to pretilt liquid crystal molecules of the liquid crystal layer;
   measuring pretilt angles of the liquid crystal molecules in a state where voltages are not applied to the pixel electrode and the common electrode after the electric-field exposing, and
   measuring tilt angles of the liquid crystal molecules in a state where voltages are applied to the pixel electrode and the common electrode after the electric field exposing,
   wherein:
   the measuring the pretilt angles includes determining whether the measured pretilt angles are within a predetermined range, and
   when the measured pretilt angles exceed the predetermined range, the method further includes analyzing pretilt angle influencing factors.

2. The method of claim 1, further comprising:
   fluorescence-exposing the liquid crystal layer after the measuring the tilt angles.

3. The method of claim 1, further comprising:
   attaching polarizers to the lower display substrate and the upper display substrate after the measuring the tilt angles.

4. The method of claim 1, wherein:
   the pretilt angle influencing factors includes a voltage intensity during the electric-field exposing, a light intensity during the electric-field exposing, and a width of a fine branch portion of the pixel electrode.

5. The method of claim 1, wherein:
   the analyzing the pretilt angle influencing factors includes analyzing an influence degree of the pretilt angle influencing factors and selecting an imputation process, and
   the method further includes notifying an analysis result of the influence degree to the imputation process.

6. A method of manufacturing a liquid crystal display device, the method comprising:
   forming field generating electrodes including a pixel electrode and a common electrode on at least one of a lower display substrate and an upper display substrate;
   forming alignment layers on the lower display substrate and the upper display substrate;
   forming a liquid crystal layer including liquid crystal molecules between the lower display substrate and the upper display substrate;
   electric-field exposing the liquid crystal layer to pretilt liquid crystal molecules of the liquid crystal layer;
   measuring pretilt angles of the liquid crystal molecules in a state where voltages are not applied to the pixel electrode and the common electrode after the electric-field exposing, and
   measuring tilt angles of the liquid crystal molecules in a state where voltages are applied to the pixel electrode and the common electrode after the electric field exposing,
   wherein:
   the measuring the tilt angles includes determining whether the measured tilt angles are within a predetermined range, and
   when the measured tilt angles exceed the predetermined range, the method further includes analyzing tilt angle influencing factors.

7. The method of claim 6, wherein:
   the tilt angle influencing factors include a channel length of a thin film transistor and a thickness of the alignment layer.

8. The method of claim 6, wherein:
   the analyzing the tilt angle influencing factors includes analyzing an influence degree of the tilt angle influencing factors and selecting an imputation process, and
   the method further includes notifying an analysis result of the influence degree to the imputation process.

* * * * *